US011896416B2

(12) United States Patent
Huo et al.

(10) Patent No.: US 11,896,416 B2
(45) Date of Patent: *Feb. 13, 2024

(54) METHOD FOR CALCULATING CORONARY ARTERY FRACTIONAL FLOW RESERVE ON BASIS OF MYOCARDIAL BLOOD FLOW AND CT IMAGES

(71) Applicant: SUZHOU RAINMED MEDICAL TECHNOLOGY CO., LTD., Suzhou (CN)

(72) Inventors: Yunfei Huo, Suzhou (CN); Guangzhi Liu, Suzhou (CN); Xingyun Wu, Suzhou (CN); Zhiyuan Wang, Suzhou (CN)

(73) Assignee: SUZHOU RAINMED MEDICAL TECHNOLOGY CO., LTD., Suzhou (CN)

( * ) Notice: Subject to any disclaimer, the term of this patent is extended or adjusted under 35 U.S.C. 154(b) by 411 days.

This patent is subject to a terminal disclaimer.

(21) Appl. No.: 17/328,550

(22) Filed: May 24, 2021

(65) Prior Publication Data

US 2021/0275124 A1 Sep. 9, 2021

Related U.S. Application Data

(63) Continuation of application No. PCT/CN2019/071203, filed on Jan. 10, 2019.

(30) Foreign Application Priority Data

Nov. 28, 2018 (CN) .......................... 201811438744.6

(51) Int. Cl.
*G06T 7/155* (2017.01)
*A61B 6/00* (2006.01)
(Continued)

(52) U.S. Cl.
CPC .............. *A61B 6/507* (2013.01); *A61B 6/032* (2013.01); *A61B 6/5217* (2013.01);
(Continued)

(58) Field of Classification Search
CPC ....... A61B 6/507; A61B 6/032; A61B 6/5217; A61B 6/5235; A61B 6/5247; A61B 6/503;
(Continued)

(56) References Cited

U.S. PATENT DOCUMENTS 9,974,508 B2 5/2018 Kassab et al.
2014/0249399 A1* 9/2014 Sharma ................. G06T 7/0012
600/407

FOREIGN PATENT DOCUMENTS

CN 104036107 A 9/2014
CN 106023202 A 10/2016
(Continued)

OTHER PUBLICATIONS

ISR for International Application PCT/CN2019/071203 dated Aug. 2, 2019.
(Continued)

*Primary Examiner* — Stephen P Coleman
(74) *Attorney, Agent, or Firm* — Ladas & Parry LLP

(57) ABSTRACT

A method for calculating coronary artery fractional flow reserve includes determining myocardial volume by extracting myocardial images; locating a coronary artery inlet and accurately segmenting coronary arteries; generating a grid model required for calculation by edge detection of coronary artery volume data; determining myocardial blood flow in a rest state and CFR by non-invasive measurement; calculating the total flow at the coronary artery inlet in a maximum hyperemia state; determining the flow in different blood vessels in the coronary artery tree in the maximum hyper-
(Continued)

emia state and then determining flow velocity $V_1$ in the maximum hyperemia state; using $V_1$ as the flow velocity at the coronary artery inlet and calculating a pressure drop $\Delta P$ from the coronary artery inlet to a distal end of a coronary stenosis, and a mean intracoronary pressure Pd at the distal end of the stenosis $P_d=P_a-\Delta P$, and calculating fractional flow reserve.

9 Claims, 4 Drawing Sheets

(51) Int. Cl.
| | | |
|---|---|---|
| *G16H 50/30* | (2018.01) | |
| *G16H 30/40* | (2018.01) | |
| *A61B 6/03* | (2006.01) | |
| *G06T 11/00* | (2006.01) | |

(52) U.S. Cl.
CPC .......... *A61B 6/5235* (2013.01); *A61B 6/5247* (2013.01); *G06T 7/155* (2017.01); *G06T 11/008* (2013.01); *G16H 30/40* (2018.01); *G16H 50/30* (2018.01); *G06T 2207/10081* (2013.01); *G06T 2207/20156* (2013.01); *G06T 2207/30104* (2013.01); *G06T 2211/412* (2013.01)

(58) Field of Classification Search
CPC ........... A61B 6/504; A61B 5/026; A61B 6/03; G06T 7/155; G06T 11/008; G06T 2207/10081; G06T 2207/20156; G06T 2207/30104; G06T 2211/412; G06T 2211/404; G06T 7/11; G06T 7/187; G06T 2207/30048; G06T 7/0012; G16H 30/40; G16H 50/30; G16H 50/50
USPC ........................................................ 382/131
See application file for complete search history.

(56) References Cited

FOREIGN PATENT DOCUMENTS

| | | |
|---|---|---|
| CN | 106473731 A | 3/2017 |
| CN | 108348206 A | 7/2018 |
| CN | 108550189 A | 9/2018 |

OTHER PUBLICATIONS

Office Action of CN application 201811438744.6 dated Feb. 3, 2021 and an English Translation.
CN 106023202 A _ English Translation.
CN 108550189 A _ English Translation.
CN 104036107 A _ English Translation.
CN 108348206 A _ English Translation.
CN 106473731 A _ English Translation.
Chinese Encyclopedia of Medicine Cardiology, Kao Run-lin, Peking Union Medical College Press, pp. 81-84, Jul. 2017.

\* cited by examiner

The present disclosure relates to the field of coronary artery imaging evaluation, and in particular to, a method for calculating coronary artery fractional flow reserve based on myocardial blood flow and CT image.

METHOD FOR CALCULATING CORONARY ARTERY FRACTIONAL FLOW RESERVE ON BASIS OF MYOCARDIAL BLOOD FLOW AND CT IMAGES

RELATED APPLICATION INFORMATION

This application is a CONTINUATION of International Application PCT/CN2019/071203 filed Jan. 10, 2019, and which claims priority from Chinese Application No. 201811438744.6 filed Nov. 28, 2018, the disclosures of which are incorporated in their entirety by reference herein.

TECHNICAL FIELD

The present disclosure relates to the field of coronary artery imaging evaluation, and in particular to, a method for calculating coronary artery fractional flow reserve based on myocardial blood flow and CT image.

BACKGROUND

Coronary angiography and intravascular ultrasound are considered to be a "gold standard" for the diagnosis of coronary heart disease, but they can only be used for imaging evaluation on stenosis degree of lesion, and it is unknown how much influence the stenosis has on distal blood flow. Fractional flow reserve (FFR) has now become a recognized indicator for functional evaluation on coronary artery stenosis, and its most important function is to accurately evaluate functional consequences of an unknown impact of coronary artery stenosis.

Fractional flow reserve (FFR) refers to a ratio of the maximum blood flow that can be obtained in the myocardial area supplied by the target vessel to be measured in the case of coronary artery stenosis to the normal maximum blood flow that can be obtained theoretically in the same area. FFR is mainly obtained by calculating a ratio of a pressure at the stenosed distal end of coronary artery to a pressure at an aortic root. The pressure at the stenosed distal end can be measured by a pressure guide wire in the maximum perfusion blood flow (measured by intracoronary or intravenous injection of papaverine or adenosine or ATP). It can be simplified as a ratio of a mean intracoronary pressure ($P_d$) at the distal end of the stenosis to a mean aortic pressure ($P_a$) at a coronary artery inlet in a maximum myocardial hyperemia state, that is, $FFR=P_d/P_a$.

Coronary CTA can accurately assess the stenosis degree of coronary artery, distinguish the nature of plaque on the wall, is a non-invasive and easy-to-operate diagnostic method for coronary artery disease and can be used as the first choice for screening high-risk population. Therefore, if intervention is performed on the blood vessels of patients with coronary heart disease, the patients' coronary arteries should be evaluated by CTA in the early stage.

The non-invasive FFR (CTFFR) calculated by the coronary CTA does not require additional imaging examination or drugs, which can fundamentally avoid unnecessary coronary angiography and revascularization treatments. The results of the DeFacto test also clearly show that in coronary CT, the analysis of CTFFR results provides physiological information of lesions that really restrict blood flow and increase the risk of the patients. CTFFR combines the advantages of coronary CTA and FFR, and can evaluate coronary artery stenosis in terms of structure and function, and becomes a new non-invasive detection system that provides anatomical and functional information of coronary artery disease. However, because CTA cannot measure the coronary flow velocity in a hyperemia state, it can only provide prediction by numerical methods, which greatly limits the clinical application of CTFFR.

SUMMARY

In order to solve the above technical problems, an object of the present disclosure is to provide a method for calculating coronary artery fractional flow reserve based on myocardial blood flow and CT image, which determines the myocardial blood flow in a rest state and the coronary flow reserve (CFR) through non-invasive measurement, and then determines flow in different blood vessels in a coronary artery tree in a maximum hyperemia state and then determines a flow velocity $V_1$ in the maximum hyperemia state, thereby quickly, accurately and fully automatically obtaining fractional flow reserve FFR.

The technical solution of the present disclosure is to provide a method for calculating coronary artery fractional flow reserve based on myocardial blood flow and CT image, comprising the following steps:

S01: segmenting the CT image of heart, obtaining an image of heart via a morphological operation, subjecting the image of heart to a histogram analysis to obtain an image contains ventricular and atrial, obtaining a myocardial image by making a difference between the image of heart and the image contains ventricular and atrial, determining a myocardial volume by the myocardial image;

S02: obtaining a full aortic complementary image by processing an aortic image, obtaining the aortic image containing a coronary artery inlet through regional growth of the full aortic complementary image, and obtaining an image containing the coronary artery inlet according to the aortic image containing the coronary artery inlet and the full aortic complementary image to determine the coronary artery inlet by the image containing the coronary artery inlet;

S03: extracting a coronary artery through regional growth by taking the coronary artery inlet as a seed point on the myocardial image, calculating an average gray and average variance of the coronary artery, and along a direction of the coronary artery, extracting a coronary artery tree according to a gray distribution of the coronary artery;

S04: binarizing the coronary artery image, drawing an isosurface image to obtain a three-dimensional grid image of the coronary artery.

S05: calculating a total flow at the coronary artery inlet in a maximum hyperemia state, $Q_{total}$=myocardial volume×myocardial blood flow×CFR, and CFR being coronary flow reserve;

S06: calculating a blood flow velocity $V_1$ in a hyperemia state;

S07: calculating a pressure drop $\Delta P$ from the coronary artery inlet to a distal end of a coronary artery stenosis using $V_1$ as an inlet flow velocity of coronary artery stenosis blood vessel, and using $P_d=P_a-\Delta P$ calculating a mean intracoronary pressure $P_d$ at the distal end of the coronary artery stenosis, wherein $P_a$ is a mean aortic pressure, and obtaining the coronary artery fractional flow reserve using $FFR=P_d/P_a$.

In the preferred technical solution, after obtaining the image containing the coronary artery inlet in step S02, the image containing the coronary artery inlet is subjected to a connected domain analysis, and each connected domain is identified by different gray labels to determine the coronary artery inlet.

In the preferred technical solution, in step S02, based on a feature that an aortic cross-section is circular, an ascending aortic and a center line are extracted from the image of heart to obtain the aortic image.

In the preferred technical solution, binarizing the coronary artery image in step S04 comprises: going through voxels in the coronary artery image, and remaining a pixel value unchanged if a voxel pixel is equal to 0; and setting the pixel value to 1 to obtain new data $V_2$ if the voxel pixel is not equal to 0.

In the preferred technical solution, in step S05, myocardial blood flow in a rest state and coronary flow reserve (CFR) are determined by cardiac ultrasound (MCE) or single photon emission computed tomography (SPECT) or positron emission tomography (PET) or cardiac nuclear magnetic (MRI) or CT perfusion.

In the preferred technical solution, step S06 comprises:

Step S61: determining a blood flow in any one of blood vessels in the tree using $Q=Q_{total}(V/V_{total})^{3/4}$ based on a flow volume scale and a cardiac surface coronary artery tree, the cardiac surface coronary artery tree obtained using a three-dimensional reconstruction of a cardiac CT, wherein $V_{total}$ is a sum volume of blood in all cardiac surface coronary artery obtained using the three-dimensional reconstruction of the cardiac CT, V is a sum volume of blood in any one of blood vessels and its downstream blood vessel in the cardiac surface coronary artery tree;

S62: determining the blood flow velocity in any one of blood vessel in the tree using $V_1=Q/D$ based on the flow volume scale and the cardiac surface coronary artery tree obtained using the three-dimensional reconstruction of the cardiac CT, wherein D is an average diameter of the blood vessel.

In the preferred technical solution, step S07 specifically comprises:

Solving three-dimensional grids of blood vessels, and solving a continuity and Navier-Stokes equations using numerical methods:

$$\nabla \cdot \vec{V} = 0 \quad [A1]$$

$$\rho \frac{\partial \vec{V}}{\partial t} + \rho \vec{V} \cdot \nabla \vec{V} = -\nabla P + V \cdot \mu \left( \nabla \vec{V} + (\nabla \vec{V})^T \right). \quad [A2]$$

Wherein, $\vec{V}$, P, $\rho$, $\mu$ are flow velocity, pressure, blood flow density, blood flow viscosity, respectively.

An inlet boundary condition is: the inlet flow velocity $V_1$ of the coronary stenosis vessel in the maximum hyperemia state.

Calculating a pressure drop of each coronary artery stenosis through three-dimensional computational fluid dynamics to obtain $\Delta P_1$, $\Delta P_2$, $\Delta P_3$ . . . , calculating the pressure drop from the coronary artery inlet to the distal end of the coronary artery stenosis using $\Delta P = \Sigma \Delta P_i$ (i=1, 2, 3 . . . ), and obtaining the mean intracoronary pressure $P_d$ at the distal end of the stenosis using $P_d = P_a - \Delta P$, wherein $P_a$ is the mean aortic pressure.

In the preferred technical solution, step S07 comprises: based on the geometric structure reconstructed by CT, straightening blood vessel with stenosis, constructing a two-dimensional axisymmetric model, dividing two-dimensional grids, and solving a continuity and Navier-Stokes equation by numerical methods:

$$\frac{1}{r}\frac{\partial}{\partial r}(r u_r) + \frac{\partial u_z}{\partial z} = 0 \quad [A3]$$

$$\rho \left( \frac{\partial u_r}{\partial t} + u_r \frac{\partial u_r}{\partial r} + u_z \frac{\partial u_r}{\partial z} \right) = -\frac{\partial p}{\partial r} + \mu \left[ \frac{1}{r}\frac{\partial}{\partial r}\left(r \frac{\partial u_r}{\partial r}\right) + \frac{\partial^2 u_r}{\partial z^2} - \frac{u_r}{r^2} \right] \quad [A4]$$

$$\rho \left( \frac{\partial u_z}{\partial t} + u_r \frac{\partial u_z}{\partial r} + u_z \frac{\partial u_z}{\partial z} \right) = -\frac{\partial p}{\partial z} + \mu \left[ \frac{1}{r}\frac{\partial}{\partial r}\left(r \frac{\partial u_z}{\partial r}\right) + \frac{\partial^2 u_z}{\partial z^2} \right] \quad [A5]$$

Wherein, $\rho$ represents the density of blood, $u_z$ and $u_r$ represent the flow velocity in the z direction and r direction, respectively, $\mu$ represents the dynamic viscosity of the blood, and p represents the pressure of the blood.

An inlet boundary condition is: the inlet flow velocity $V_1$ of the coronary stenosis vessel in the maximum hyperemia state.

Calculating a pressure drop of each coronary artery stenosis through two-dimensional computational fluid dynamics to obtain $\Delta P_1$, $\Delta P_2$, $\Delta P_3$ . . . , calculating the pressure drop from the coronary artery inlet to the distal end of the coronary stenosis using $\Delta P = \Sigma \Delta P_i$ (i=1, 2, 3 . . . ), and obtaining the mean intracoronary pressure $P_d$ at the distal end of the stenosis using $P_d = P_a - \Delta P$, wherein $P_a$ is the mean aortic pressure.

In the preferred technical solution, step S07 also comprises: as for different types of bends of the blood vessels, calculating a pressure difference from the inlet to an outlet using a three-dimensional model; in comparison with a calculation of two-dimensional axisymmetric model, establishing a correction coefficient database, which is used to store coefficients for correcting the two-dimensional axisymmetric results through various types of bending.

After obtaining the pressure, obtaining a corrected pressure difference from the inlet to the outlet with reference to the correction coefficients in the database, and then calculating FFR by the corrected pressure difference.

Compared with the prior art, the advantages of the present disclosure comprise that fractional flow reserve FFR can be obtained quickly, accurately and fully automatically through myocardial blood flow and CT image of heart, the accuracy of the existing CTFFR (or FFRCT) has been improved greatly in the present disclosure. Difficulties and risks of surgeries are greatly reduced due to non-invasive measurement, the non-invasive measurement is easy to operate and thus can be widely used in clinical applications.

BRIEF DESCRIPTION OF DRAWINGS

The present disclosure will be further described below with reference to the drawings and embodiments.

DETAILED DESCRIPTION OF PREFERRED EMBODIMENTS

In order to make purposes, technical solutions and advantages of the disclosure clearer, the present disclosure will be described in detail below in conjunction with the specific embodiments and the corresponding accompanying drawings. It should be understood that these descriptions are only exemplary and are not intended to limit the scope of the present disclosure. In addition, in the following description, descriptions of well-known structures and technologies are omitted to avoid unnecessary confusion of the concepts of the present disclosure.

Given a CT image of heart, the image of the heart is extracted and obtained by extracting the heart according to a reverse method, and processing descending aorta, spine, and ribs in non-target areas as objects, and gradually removing non-heart tissues, such as chest walls, lungs, vertebrae, and descending aorta. Based on a feature of cross section of the aorta to be circular, ascending aorta and center line are extracted from the obtained image of heart to obtain the aortic image.

Figure 1:
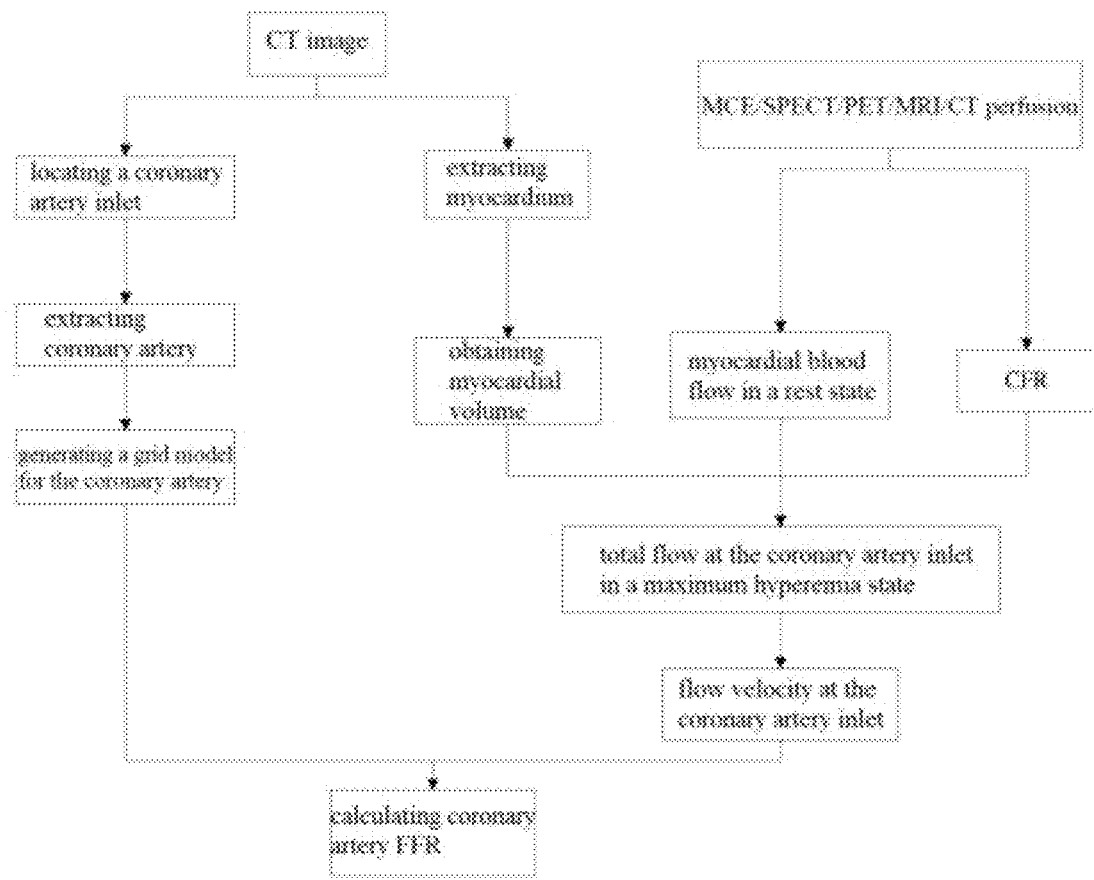
FIG. 1 is a flow chart of a method of the present disclosure.
Figure 2:
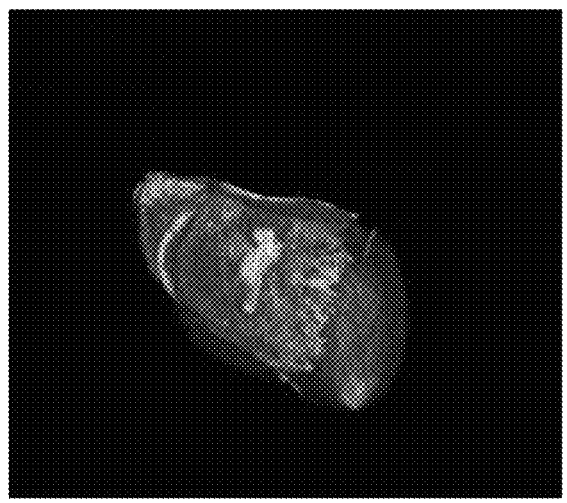
FIG. 2 shows results of myocardial segmentation for a CT image of heart.

As shown in FIG. 1, a method for calculating the coronary fractional flow reserve (FFR) based on myocardial blood flow and CT image of the present disclosure comprises extracting a myocardial image, extracting a coronary artery inlet, extracting coronary artery, generating a grid model for the coronary artery, and determining myocardial blood flow in a rest state and coronary flow reserve (CFR), calculating total flow at the coronary artery inlet in a maximum hyperemia state, calculating a blood flow velocity $V_1$ in the hyperemia state, and determining the coronary FFR. It specifically comprises the following steps:

1: Extracting the Myocardial Image:

The CT image of heart is segmented, the image of heart is obtained through a morphological operation, a histogram analysis is subjected to the image of heart to obtain a ventricular and atrial image, and a myocardial image is obtained by making the difference between the image of heart and the ventricular and atrial image, as shown in FIG. 2.

2: Extracting the Coronary Artery Inlet:

A morphological expansion is subjected to the binary image of the aortic image to obtain the binary image of the whole aorta, and a complementary image of the whole aorta is obtained by pixel inversion.

Figure 3:
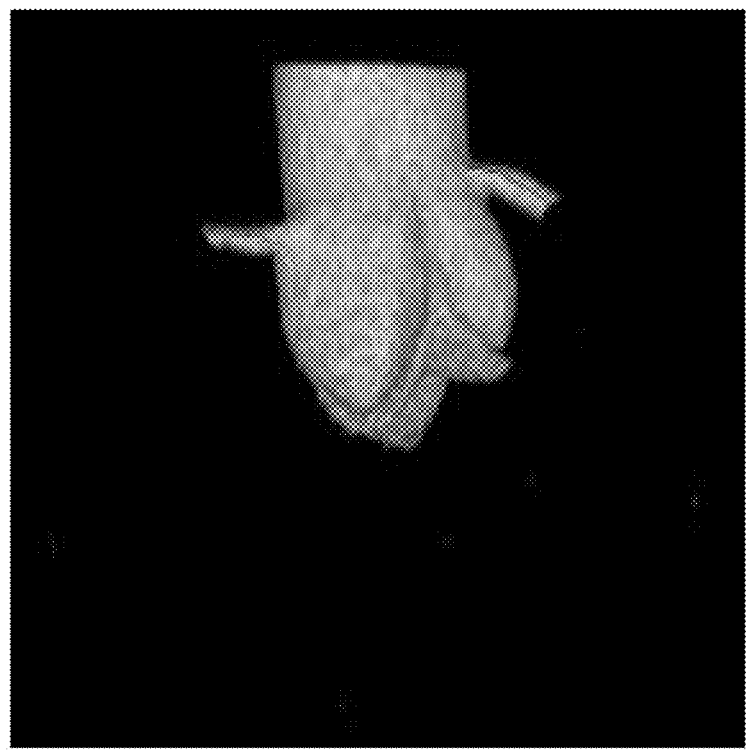
FIG. 3 shows results of aorta segmentation with a coronary artery inlet.

Regional growth is carried out according to average gray level of points on the center line of the aorta to obtain the aortic image with the coronary artery inlet, as shown in FIG. 3.

Figure 4:
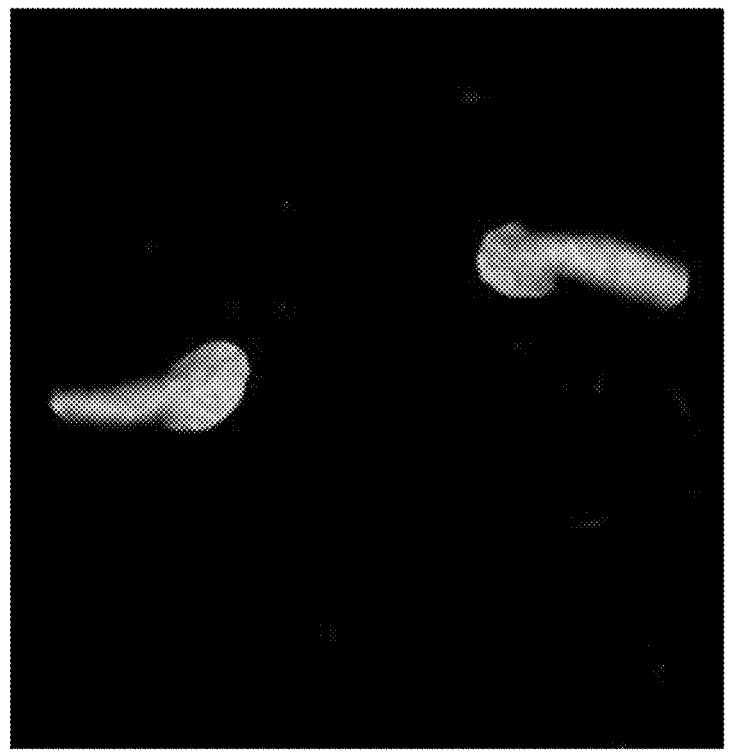
FIG. 4 shows results of coronary artery inlet segmentation.

The aortic image with the coronary artery inlet and the complementary image of the whole aorta are subjected to the graphic multiplication method to obtain an image with the coronary artery inlet. Connected domain analysis is subjected to the image with the coronary artery inlet, and each connected domain is identified by using different gray labels to determine the coronary artery inlet, as shown in FIG. 4.

Figure 5:
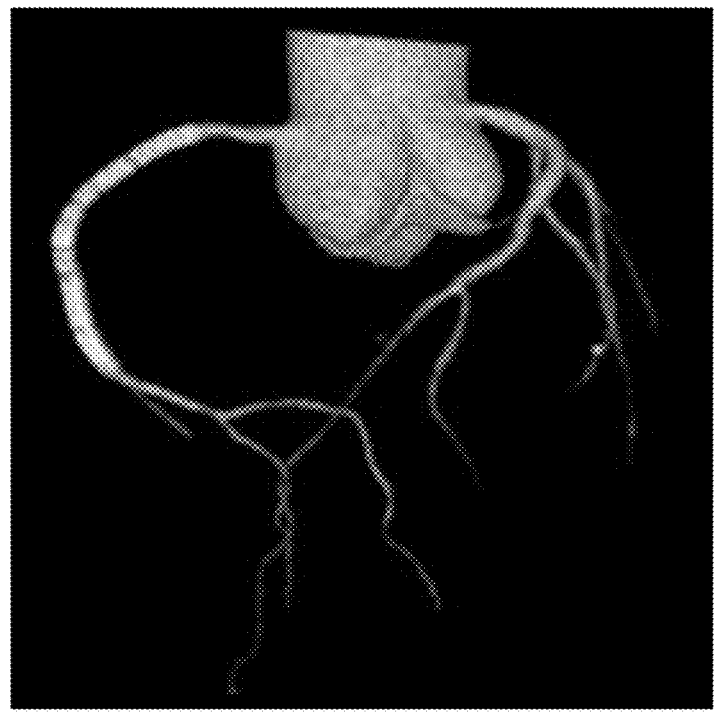
FIG. 5 shows results of coronary artery segmentation.

3: Extracting the Coronary Artery:

The coronary artery inlet is taken as a seed point on the myocardial image, the coronary artery is extracted through regional growth, an average gray and average variance of the coronary artery are calculated, and a coronary artery tree is extracted along a direction of the coronary artery according to a gray distribution of the coronary artery, as shown in the FIG. 5.

4: Generating the Grid Model for the Coronary Artery:

Image data $V_1$ of the coronary artery is obtained through step 3. The voxels in the data spatially form a cube. A pixel value of the voxel belonging to the coronary artery is not 0 (the pixel value is approximately between −3000 and 3000), and pixel values of the remaining voxels are all 0.

In this step, the data needs to be transformed into spatial three-dimensional grid data V3 to facilitate FFR calculation in step 5.

(1) Binarization of Coronary Artery Data

The voxels in the image data V1 of the coronary artery are went through and a simple judgment for pixel values is made. If pixel A1 is equal to 0, the pixel value remains unchanged; if A1 is not equal to 0, the pixel value of A1 is set to 1.

Finally, a new image data V2 will be obtained. In this image, the pixel value of voxels belonging to part of the coronary artery is 1, and the rest is 0.

(2) Generation of Isosurface

A voxel is defined as a tiny hexahedron with eight vertices on a cube composed of four pixels between adjacent upper and lower layers. The isosurface is a collection of points with the same attribute value in space. It can be expressed as:

$$\{(x,y,z)|f(x,y,z)=c\}, c \text{ is a constant.}$$

In this method, c is the pixel value 1 given in the three-dimensional reconstruction process.

The process of extracting the isosurface is as follows:
(1) reading the preprocessed original data into a specific array;
(2) extracting a unit body from the grid data body to become the current unit body, and at the same time obtaining all information of the unit body;
(3) comparing the function values of the 8 vertices of the current unit body with the given isosurface value C to obtain a state table of the unit body;
(4) according to a state table index of the current unit body, finding out the edge of the unit body intersecting with the isosurface, and using linear interpolation method to calculate the position coordinates of each intersection;
(5) using the center difference method to find the normal vectors of the 8 vertices of the current unit body, and then using the linear interpolation method to obtain the normal directions of each vertex of the triangle face;
(6) drawing an image of the isosurface according to the coordinates of the vertices of each triangle face and the normal vector of the vertices.

Figure 6:
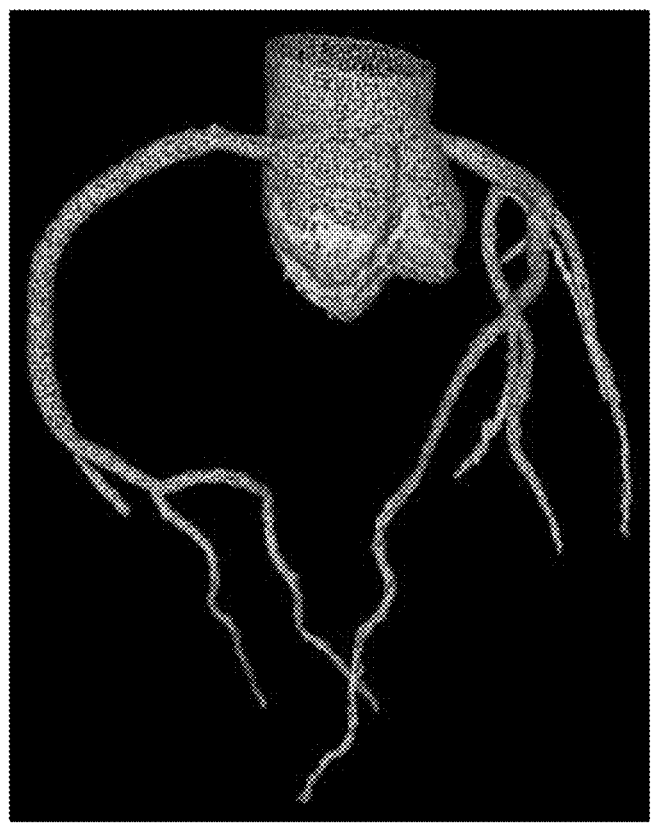
FIG. 6 is a grid model for the results of the coronary artery segmentation.

Finally, three-dimensional grid image data V3 of the coronary artery is obtained, as shown in FIG. 6.

Figure 7:
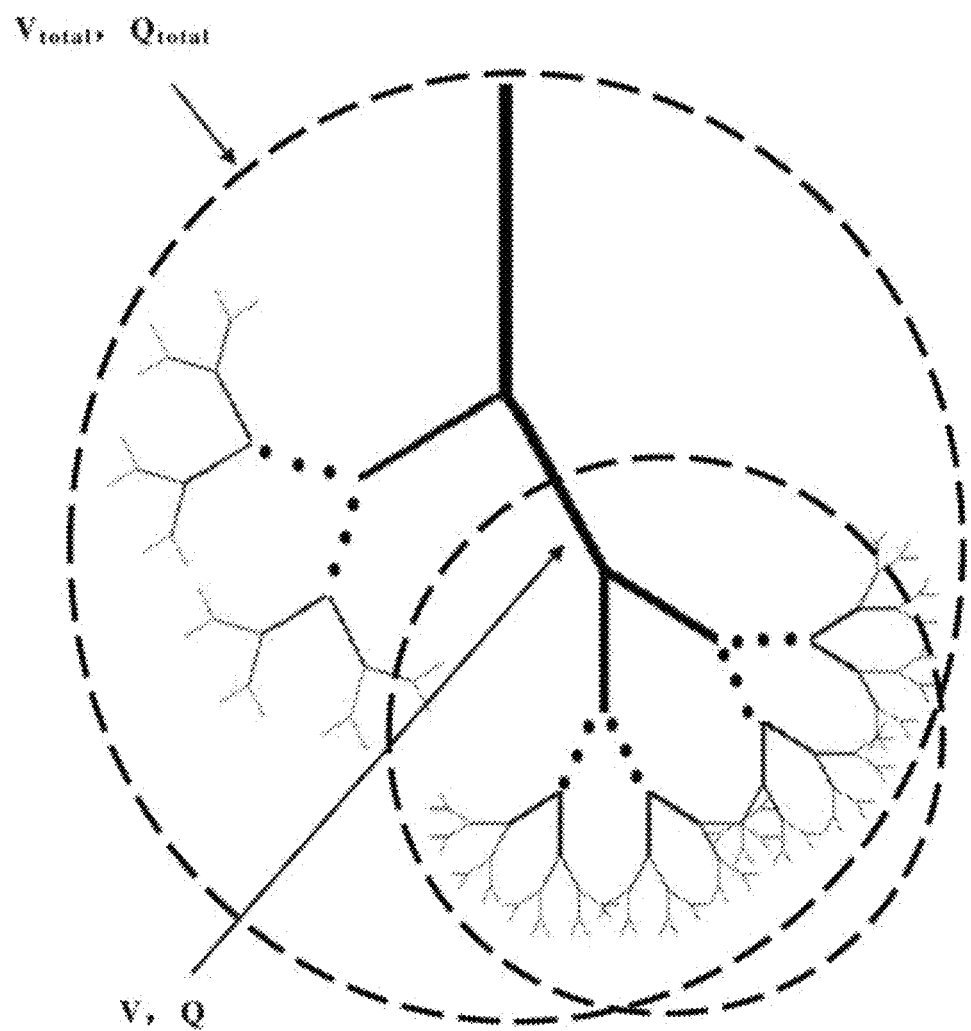
FIG. 7 is a schematic diagram of blood flow of the heart and coronary artery.

5: Calculating the Blood Flow Velocity $V_1$ in the Hyperemia State:

The myocardial blood flow in a rest state and coronary flow reserve (CFR) are determined by non-invasive measurements such as cardiac ultrasound (MCE) or single photon emission computed tomography (SPECT) or positron emission tomography (PET) or cardiac nuclear magnetic (MRI) or CT perfusion; the total flow at the coronary artery inlet (including the sum of the left coronary artery tree and the right coronary artery tree) in the maximum hyperemia state is calculated: $Q_{total}$=myocardial volume×myocardial blood flow×CFR;

Based on a flow volume scale and a cardiac surface coronary artery tree obtained using a three-dimensional reconstruction of a cardiac CT, the blood flow Q in any one of blood vessels in the tree is determined: $Q=Q_{total}(V/V_{total})^{3/4}$, wherein $V_{total}$ is a sum volume of blood in all cardiac surface coronary artery obtained using the three-dimensional reconstruction of the cardiac CT, V is a sum volume of blood in any one of blood vessels and its downstream vessel in the cardiac surface coronary artery tree, as shown in FIG. 7; based on the flow volume scale and the cardiac surface coronary artery tree obtained using the three-dimensional reconstruction of the cardiac CT, a blood flow velocity in any one of blood vessels in the tree is determined: $V_1=Q/D$, wherein D is average diameter of the blood vessel (the blood volume of the blood vessel divided by the length of the blood vessel).

6: Calculating Coronary FFR:

A pressure drop of each coronary artery stenosis is calculated through computational fluid dynamics (CFD) using $V_1$ as the inlet flow velocity of the coronary stenosis vessel to obtain $\Delta P_1, \Delta P_2, \Delta P_3 \ldots$, the pressure drop from the coronary artery inlet to a distal end of the coronary artery stenosis is calculated using $\Delta P=\Sigma \Delta P_i$ (i=1, 2, 3 . . . ), and the mean intracoronary pressure $P_d$ at the distal end of the stenosis is obtained using $P_d=P_a-\Delta P$, wherein $P_a$ is the mean aortic pressure, and finally the fractional flow reserve is calculated by the formula $FFR=P_d/P_a$.

The processing steps for the 3D model comprise:

Based on the geometric structure reconstructed by CT, dividing three-dimensional grids, and using numerical methods (such as: finite difference, finite element, finite volume method, etc.) to solve the continuity and Navier-Stokes equations:

$$\nabla \cdot \vec{V}=0 \qquad [A1]$$

$$\rho\frac{\partial \vec{V}}{\partial t} + \rho \vec{V} \cdot \nabla \vec{V} = -\nabla P + V \cdot \mu\left(\left(\nabla \vec{V} + \left(\nabla \vec{V}\right)^T\right)\right) \qquad [A2]$$

Wherein, $\vec{V}, P, \rho, \mu$ are flow velocity, pressure, blood flow density, blood flow viscosity, respectively.

The inlet boundary condition is: the inlet flow velocity V1 of the coronary stenosis vessel in the maximum hyperemia state.

Based on formula [A1] and [A2], a pressure drop of each coronary artery stenosis is calculated by carrying out three-dimensional CFD to obtain $\Delta P_1, \Delta P_2, \Delta P_3 \ldots$, the pressure drop from the coronary artery inlet to a distal end of the coronary artery stenosis is calculated using $\Delta P=\Sigma \Delta P_i$ (i=1, 2, 3 . . . ), and the mean intracoronary pressure $P_d$ at the distal end of the stenosis is obtained using $P_d=P_a-\Delta P$, wherein $P_a$ is the mean aortic pressure.

For the two-dimensional model, the following steps are included:

Based on the geometric structure reconstructed by CT, straightening the blood vessel with stenosis (two-dimensional axisymmetric model), dividing two-dimensional grids, and using numerical methods (such as finite difference, finite element, finite volume method, etc.) to solve a continuity and Navier-Stokes equation:

$$\frac{1}{r}\frac{\partial}{\partial r}(ru_r) + \frac{\partial u_z}{\partial z} = 0 \qquad [A3]$$

$$\rho\left(\frac{\partial u_r}{\partial t} + u_r\frac{\partial u_r}{\partial r} + u_z\frac{\partial u_r}{\partial z}\right) = -\frac{\partial p}{\partial r} + \mu\left[\frac{1}{r}\frac{\partial}{\partial r}\left(r\frac{\partial u_r}{\partial r}\right) + \frac{\partial^2 u_r}{\partial z^2} - \frac{u_r}{r^2}\right] \qquad [A4]$$

$$\rho\left(\frac{\partial u_z}{\partial t} + u_r\frac{\partial u_z}{\partial r} + u_z\frac{\partial u_z}{\partial z}\right) = -\frac{\partial p}{\partial z} + \mu\left[\frac{1}{r}\frac{\partial}{\partial r}\left(r\frac{\partial u_z}{\partial r}\right) + \frac{\partial^2 u_z}{\partial z^2}\right] \qquad [A5]$$

Wherein, $\rho$ represents the density of blood, $u_z$ and $u_r$ represent the flow velocity in the z direction and r direction, respectively, $\mu$ represents the dynamic viscosity of the blood, and p represents the pressure of the blood.

The inlet boundary condition is: the inlet flow velocity $V_1$ of the coronary stenosis vessel in the maximum hyperemia state.

Based on the formula [A3]-[A5], a pressure drop of each coronary artery stenosis is calculated by carrying out two-dimensional CFD to obtain $\Delta P_1, \Delta P_2, \Delta P_3 \ldots$, the pressure drop from the coronary artery inlet to a distal end of the coronary artery stenosis is calculated using $\Delta P=\Sigma \Delta P_i$ (i=1, 2, 3 . . . ), and the mean intracoronary pressure Pd at the distal end of the stenosis is obtained using $P_d=P_a-\Delta P$, wherein $P_a$ is the mean aortic pressure.

As for different types of bending of the blood vessels, pressure difference from the inlet to the outlet is calculated by using the three-dimensional model, and the calculation is made by comparing with the two-dimensional axisymmetric model to establish a correction coefficient database, which is used to store coefficients for correcting the two-dimensional axisymmetric results through various types of bending; the pressure is calculated and then the corrected pressure difference from the inlet to the outlet is obtained by comparing with the correction coefficients in the database, and FFR is finally calculated by the formula.

It should be understood that the specific embodiments mentioned above are merely intended to exemplify or explain of the principles of the present disclosure and not to be limitations to the present disclosure. Therefore, any modifications, equivalent substitutions, improvements and the like made without departing from the spirit and scope of the present disclosure should be included in the protection scope of the present disclosure. In addition, the appended claims of the present disclosure are intended to cover all changes and modifications falling within the scope and boundary of the appended claims, or equivalents of such scope and boundary.

What is claimed is:

1. A method for calculating coronary artery fractional flow reserve based on myocardial blood flow and CT image, comprising the following steps:

S01: segmenting the CT image of heart, obtaining an image of heart via a morphological operation, subjecting the image of heart to a histogram analysis to obtain an image contains ventricular and atrial, obtaining a myocardial image by making a difference between the image of heart and the image contains ventricular and atrial, determining a myocardial volume by the myocardial image;

S02: obtaining a full aortic complementary image by processing an aortic image, obtaining the aortic image containing a coronary artery inlet through regional growth of the full aortic complementary image, and obtaining an image containing the coronary artery inlet according to the aortic image containing the coronary artery inlet and the full aortic complementary image to determine the coronary artery inlet by the image containing the coronary artery inlet;

S03: extracting a coronary artery through regional growth by taking the coronary artery inlet as a seed point on the myocardial image, calculating an average gray and average variance of the coronary artery, and along a direction of the coronary artery, extracting a coronary artery tree according to a gray distribution of the coronary artery;

S04: binarizing the coronary artery image, drawing an isosurface image to obtain a three-dimensional grid image of the coronary artery;

S05: calculating a total flow at the coronary artery inlet in a maximum hyperemia state, $Q_{total}$=myocardial volume×myocardial blood flow×CFR, and CFR being the coronary flow reserve;

S06: calculating a blood flow velocity $V_1$ in a hyperemia state;

S07: calculating a pressure drop $\Delta P$ from the coronary artery inlet to a distal end of a coronary artery stenosis using $V_1$ as an inlet flow velocity of coronary artery stenosis blood vessel, using $P_d=P_a-\Delta P$ calculating a mean intracoronary pressure $P_d$ at the distal end of the coronary artery stenosis, wherein $P_a$ is a mean aortic pressure, and obtaining the fractional flow reserve using $FFR=P_d/P_a$.

2. The method for calculating coronary artery fractional flow reserve based on myocardial blood flow and CT image according to claim 1, wherein after obtaining the image containing the coronary artery inlet in step S02, the image containing the coronary artery inlet is subjected to a connected domain analysis, and each connected domain is identified by different gray labels to determine the coronary artery inlet.

3. The method for calculating coronary artery fractional flow reserve based on myocardial blood flow and CT image according to claim 1, wherein in step S02, based on a feature that an aortic cross-section is circular, an ascending aortic and a center line are extracted from the image of heart to obtain the aortic image.

4. The method for calculating coronary artery fractional flow reserve based on myocardial blood flow and CT image according to claim 1, wherein binarizing the coronary artery image in step S04 comprises: going through voxels in the coronary artery image, remaining a pixel value unchanged if a voxel pixel is equal to 0; and setting the pixel value to 1 to obtain new data if the voxel pixel is not equal to 0.

5. The method for calculating coronary artery fractional flow reserve based on myocardial blood flow and CT image according to claim 1, wherein in step S05, myocardial blood flow in a rest state and coronary flow reserve (CFR) are determined by cardiac ultrasound (MCE) or single photon emission computed tomography (SPECT) or positron emission tomography (PET) or cardiac nuclear magnetic (MRI) or CT perfusion.

6. The method for calculating coronary artery fractional flow reserve based on myocardial blood flow and CT image according to claim 1, wherein step S06 comprises:

S61: determining a blood flow in any one of blood vessels in the tree using $Q=Q_{total}\times(V/V_{total})^{3/4}$ based on a flow volume scale and a cardiac surface coronary artery tree obtained using a three-dimensional reconstruction of a cardiac CT, wherein $V_{total}$ is a sum volume of blood in all cardiac surface coronary artery obtained using the three-dimensional reconstruction of the cardiac CT, V is a sum volume of blood in any one of blood vessels and its downstream blood vessel in the cardiac surface coronary artery tree;

S62: determining the blood flow velocity in any one of blood vessel in the tree using $V_1=Q/D$ based on the flow volume scale and the cardiac surface coronary artery tree obtained using the three-dimensional reconstruction of the cardiac CT, wherein D is an average diameter of the blood vessel.

7. The method for calculating coronary artery fractional flow reserve based on myocardial blood flow and CT image according to claim 1, wherein step S07 specifically comprises:

solving three-dimensional grids of blood vessels, and solving a continuity and Navier-Stokes equations using numerical methods:

$$\nabla \cdot \vec{V} = 0 \quad \text{[A1]}$$

$$\rho \frac{\partial \vec{V}}{\partial t} + \rho \vec{V} \cdot \nabla \vec{V} = -\nabla P + \nabla \cdot \mu \left( \nabla \vec{V} + \left( \nabla \vec{V} \right)^T \right) \quad \text{[A2]}$$

wherein, $\vec{V}$, P, $\rho$, $\mu$ are flow velocity, pressure, blood flow density, blood flow viscosity, respectively;

an inlet boundary condition being: the inlet flow velocity $V_1$ of the coronary stenosis vessel in the maximum hyperemia state;

calculating a pressure drop of each coronary artery stenosis through three-dimensional computational fluid dynamics to obtain $\Delta P_1$, $\Delta P_2$, $\Delta P_3$ ..., calculating the pressure drop from the coronary artery inlet to the distal end of the coronary artery stenosis using $\Delta P = \Sigma \Delta P_i$ (i=1, 2, 3 ...), and obtaining the mean intracoronary pressure $P_d$ at the distal end of the stenosis using $P_d=P_a-\Delta P$, wherein $P_a$ is the mean aortic pressure.

8. The method for calculating coronary artery fractional flow reserve based on myocardial blood flow and CT image according to claim 1, wherein step S07 comprises:

based on the geometric structure reconstructed by CT, straightening blood vessel with stenosis, constructing a two-dimensional axisymmetric model, dividing two-dimensional grids, and solving a continuity and Navier-Stokes equation by numerical methods:

$$\frac{1}{r}\frac{\partial}{\partial r}(ru_r) + \frac{\partial u_z}{\partial z} = 0 \quad \text{[A3]}$$

$$\rho\left(\frac{\partial u_r}{\partial t} + u_r\frac{\partial u_r}{\partial r} + u_z\frac{\partial u_r}{\partial z}\right) = -\frac{\partial p}{\partial r} + \mu\left[\frac{1}{r}\frac{\partial}{\partial r}\left(r\frac{\partial u_r}{\partial r}\right) + \frac{\partial^2 u_r}{\partial z^2} - \frac{u_r}{r^2}\right] \quad \text{[A4]}$$

$$\rho\left(\frac{\partial u_z}{\partial t} + u_r\frac{\partial u_z}{\partial r} + u_z\frac{\partial u_z}{\partial z}\right) = -\frac{\partial p}{\partial z} + \mu\left[\frac{1}{r}\frac{\partial}{\partial r}\left(r\frac{\partial u_z}{\partial r}\right) + \frac{\partial^2 u_z}{\partial z^2}\right] \quad \text{[A5]}$$

wherein, $\rho$ represents the density of blood, $u_z$ and $u_r$ represent the flow velocity in the z direction and r direction, respectively, $\mu$ represents the dynamic viscosity of the blood, and p represents the pressure of the blood;

an inlet boundary condition being: the inlet flow velocity $V_1$ of the coronary stenosis vessel in the maximum hyperemia state;

calculating a pressure drop of each coronary artery stenosis through two-dimensional computational fluid dynamics to obtain $\Delta P_1$, $\Delta P_2$, $\Delta P_3$ . . . , calculating the pressure drop from the coronary artery inlet to the distal end of the coronary stenosis using $\Delta P = \Sigma \Delta P_i$ (i=1, 2, 3 . . . ), and obtaining the mean intracoronary pressure $P_d$ at the distal end of the stenosis using $P_d = P_a - \Delta P$, wherein $P_a$ is the mean aortic pressure.

9. The method for calculating coronary artery fractional flow reserve based on myocardial blood flow and CT image according to claim 8, wherein the step S07 further comprises: for different types of bends of the blood vessels, calculating a pressure difference from the inlet to an outlet using a three-dimensional model; in comparison with a calculation of two-dimensional axisymmetric model, establishing a correction coefficient database, which is used to store coefficients for correcting the two-dimensional axisymmetric results through various types of bending;

after obtaining the pressure, obtaining a corrected pressure difference from the inlet to the outlet with reference to the correction coefficients in the database, and then calculating FFR by the corrected pressure difference.

* * * * *